(12) United States Patent
Rzany et al.

(10) Patent No.: US 9,402,934 B2
(45) Date of Patent: Aug. 2, 2016

(54) METHOD FOR PREPARING BIOLOGICAL TISSUE (71) Applicant: BIOTRONIK AG, Buelach (CH)

(72) Inventors: Alexander Rzany, Nuremberg (DE); Wilhelm Erdbruegger, Constance (DE)

(73) Assignee: BIOTRONIK AG, Beulach (CH)

( * ) Notice: Subject to any disclaimer, the term of this patent is extended or adjusted under 35 U.S.C. 154(b) by 0 days.

(21) Appl. No.: 14/341,783

(22) Filed: Jul. 26, 2014

(65) Prior Publication Data
US 2015/0037433 A1    Feb. 5, 2015

(30) Foreign Application Priority Data

Jul. 31, 2013 (EP) .................................... 13178696

(51) Int. Cl.
*A61L 27/36* (2006.01)
*A61L 27/24* (2006.01)

(52) U.S. Cl.
CPC ............. *A61L 27/3687* (2013.01); *A61L 27/24* (2013.01); *A61L 27/367* (2013.01); *A61L 2430/20* (2013.01); *A61L 2430/40* (2013.01)

(58) Field of Classification Search
None
See application file for complete search history.

(56) References Cited

U.S. PATENT DOCUMENTS

| 5,336,616 | A | * | 8/1994 | Livesey | ..................... | A01N 1/00 |
| | | | | | | 435/1.3 |
| 2012/0189588 | A1 | * | 7/2012 | Nahas | ..................... | A61K 31/00 |
| | | | | | | 424/93.7 |
| 2013/0158676 | A1 | * | 6/2013 | Hayzlett | ..................... | A61F 2/02 |
| | | | | | | 623/23.72 |
| 2013/0190893 | A1 | * | 7/2013 | Roock | ..................... | A61F 2/02 |
| | | | | | | 623/23.72 |

OTHER PUBLICATIONS

Everaerts, F.J.L "A Novel Approach in Cross-linking of Bioprosthetic Heart Valves" Thesis, University of Twente, 2007, 150pp. ISBN:978-90-365-2536-7.*
Youngstrom DW, Barrett JG, Jose RR, Kaplan DL "Functional Characterization of Detergent-Decellularized Equine Tendon Extracellular Matrix for Tissue Engineering Applications" PLoS One, May 27, 2013, 8(5): e64151, pp. 1-9. doi:10.1371/journal.pone.0064151.*
Pratt, W.B. "Antibiotics that Affect Membrane Permeability: Polymyxin B, Colistin, and Gramicidin A" The Antimicrobial Drugs, 2000, chapter 8, pp. 234-241.*

* cited by examiner

*Primary Examiner* — Louise W Humphrey
*Assistant Examiner* — Aaron J Kosar
(74) *Attorney, Agent, or Firm* — Wagenknecht IP Law Group PC (57) ABSTRACT

A method for preparing tissue for medical applications, in particular tissue for use for an artificial heart valve, wherein the method has the steps of decellularizing the tissue by means of a detergent and subsequently cross-linking the collagen fibers of the tissue by means of a suitable cross-linking agent. At least one lipopeptide, such as surfactin, for example, is used as the detergent for decellularization.

10 Claims, 7 Drawing Sheets

STAND DER TECHNIK

FIG. 3c

STAND DER TECHNIK

METHOD FOR PREPARING BIOLOGICAL TISSUE

CROSS REFERENCE TO RELATED APPLICATIONS

This invention claims benefit of priority to European patent application EP 13178696.4, filed Jul. 31, 2013: the contents of which are herein incorporated by reference in their entirety.

FIELD OF THE INVENTION

The present invention relates to a method for preparing tissue for medical applications, in particular for preparing tissue for use for an artificial heart valve, including the steps of decellularizing the tissue by means of a suitable detergent and subsequently cross-linking the collagen fibers of the tissue by means of a suitable cross-linking agent.

BACKGROUND OF THE INVENTION

There are basically two different types of heart valve prostheses: Prostheses comprising mechanical valves, which are artificially produced, usually being made of graphite coated with pyrolytic carbon, and prostheses comprising valves made of biological tissue, usually pericardial tissue, which is usually obtained from animal sources (e.g. swine or cattle). The heart valve formed of biological tissue is usually mounted in a base body (e.g. a rigid plastic framework or a self-expanding stent), which is then implanted at the position of the natural valve. The present invention describes a method for preparing such tissue for use in a heart valve prosthesis for implantation at the site of a natural heart valve.

The tissue of origin must be thoroughly cleaned and prepared before implantation. In so doing, the tissue is modified, to the greatest extent possible, such that the tissue is not recognized by the body as foreign tissue, is not calcified, and has the longest life span possible. Such a method for preparing tissue substantially comprises at least two main steps having a plurality of intermediate rinsing processes.

The first essential preparation step is the so-called decellularization of the tissue. In this step, cell membranes, intracellular proteins, cell nuclei, and other cellular components are removed as completely as possible from the tissue in order to obtain the purest extracellular matrix possible. Any cells and cellular components remaining in the tissue would be potent crystal nuclei, in particular, for an unwanted calcification of the biological implant material. The decellularization, as a washing step, should be performed in a manner that is so gentle that the structure and the collagen fibers in the extracellular matrix remain as unaffected as possible while ensuring that all cells contained therein are thoroughly removed from the tissue.

The second essential preparation step is that of cross-linking the tissue, in particular the collagen fibers. After decellularization, preferably all cellular components have been removed from the tissue and the biological material nearly exclusively comprises the extracellular matrix. In the case of pericardial tissue, the extracellular matrix is formed primarily of collagen fibers. In order to obtain biological material having the most optimal mechanical properties possible and to prevent rejection reactions by the receiving body, the collagen fibers are cross-linked by means of a suitable cross-linking agent via the incorporation of chemical bonds. The cross-linking agent binds to the amino groups of the collagen fibers and forms chemically stable compounds between collagen fibers. A biological material having long-term stability is thereby obtained from the three-dimensionally arranged collagen fibers, wherein this biological material is no longer recognized as foreign biological material. The stability and strainability of the tissue is markedly increased by means of the three-dimensional cross-linking or linking of the individual collagen fibers via the cross-linking agent. This is decisive, in particular, in the case of use as tissue of a heart valve, where the tissue must open and close, in brief intervals, as a valve.

An alternative method for preparing biological tissue is described in WO 2004/052417. In this method according to the prior art, the tissue is decellularized with a 1-2% deoxycholic acid solution. After a plurality of rinsing steps, the tissue is conditioned in a solution containing a cyclic lipopeptide. The cyclic lipopeptide surfactin is used, in particular, as the conditioning agent after decellularization is completed and before repopulation with cells. In this alternative method according to the prior art, cross-linking of the collagen fibers is not performed using a suitable cross-linking agent. After conditioning, the tissue is populated with natural cells.

WO 2011/109433 discloses a method for preparing biological tissue, wherein distilled water is used for decellularization. Glutaraldehyde functions as the cross-linking agent in a subsequent step.

WO 2005/118014 discloses the use of a first ionic detergent and a second non-ionic detergent for decellularization. In this case, an anionic detergent such as sodium dodecyl sulfate or sodium dodecyl sulfonate is preferably provided as the first ionic detergent. As an alternative, bile acids such as sodium cholate or sodium deoxycholate can be used as the first detergent. The second detergent is electrically neutrally charged, such as a detergent containing polyethylene glycol.

SUMMARY OF THE INVENTION

The problem addressed by the present invention is therefore that of designing a method for preparing biological tissue such that cellular components are removed from the tissue in a thorough yet gentle manner such that subsequent cross-linking produces a mechanically stable and long-lived tissue, which is suitable, in particular, for use as tissue of an artificial heart valve.

A further problem addressed by the present invention is that of finding a new use for solutions that contain at least one lipopeptide.

The stated problem is solved, in terms of a method for preparing tissue for medical applications, in particular tissue for use for an artificial heart valve, including: decellularizing the tissue by means of a detergent, and subsequently cross-linking the collagen fibers of the tissue by means of a suitable cross-linking agent; characterized in that the detergent for decellularization contains at least one lipopeptide having amphiphilic properties, comprising a hydrophilic base structure and a hydrophobic side chain. The stated problem is solved, in terms of the application, by use of a solution containing at least one lipopeptide having amphiphilic properties, comprising a hydrophilic basic structure and a hydrophobic side chain, as the detergent for the decellularization of biological tissue, in particular biological tissue for heart valve prostheses. Advantageous embodiments of the inventions are described herein.

The invention is described in the following using the example of a method for preparing tissue for use for an artificial heart valve. Although the present invention is particularly suitable for preparing this type of tissue, it is not limited to this application. The present invention can also be used to prepare blood vessels, bone cartilage, ligaments, or the like.

The invention further relates to a use for at least one solution containing lipopeptides.

The fundamental concept of the invention is the use of lipopeptides as detergent for decellularization. According to the inventive concept, peptides, lipopeptides containing β-hydroxy fatty acids or β-amino fatty acids are not used for conditioning, but rather as detergent for decellularization. Surprisingly, it has been shown that lipopeptides yield excellent results in the decellularization of tissue. The tissue is freed of cellular components in a markedly more gentle manner When a detergent according to the invention is used, the structure of the extracellular matrix is retained to a markedly better extent than is the case with a detergent according to the prior art. The detergent according to the invention therefore contains at least one lipopeptide having amphiphilic properties, comprising a hydrophilic base structure and a hydrophobic side chain. As a result, the subsequent cross-linking step results in a tissue having mechanical properties that are markedly improved over the prior art and which is therefore suited for use, in particular, for use in a heart valve prosthesis.

Particularly preferably, the detergent for decellularization contains a cyclic lipoheptapeptide, in particular surfactin. In this preferred embodiment of the invention, a detergent containing surfactin is used for decellularization. In particular, the detergent contains surfactin having a cyclic structure, as indicated in the following:

Therein, n=10-12 and Glu, Leu, Val, Asp stand for the amino acids glutaminic acid, leucine, valine, and asparginic acid.

Other advantageous lipopeptides include daptomycin, caspofungin, arthrofactin, echinocandins, iturins, syringomycins, syringopeptides, and/or polymyxins. Advantageously, the detergent contains at least one lipopeptide selected from the list: Surfactin, daptomycin, caspofungin, arthrofactin, or the group of echinocandins, iturins, syringomycins, syringopeptides, polymyxins.

The cross-linking agent preferably contains glutaraldehyde. In alternative embodiments of the invention, the cross-linking agent contains carbodiimide, formaldehyde, glutaraldehyde acetals, acyl azides, cyanimide, genipin, tannin, pentagalloyl glucose, phytate, proanthocyanidin, reuterin and/or epoxide compounds.

Advantageously, the tissue is rinsed before and, particularly preferably, after decellularization at least once, preferably a plurality of times, with a suitable solvent, in particular a buffered saline solution and/or an alcohol solution. Buffered sodium chloride solutions and/or an ethanol solution are particularly advantageous.

Particularly preferably, the detergent comprises a buffer solution, particularly preferably a phosphate buffer solution, advantageously at pH 7.4, which contains the lipopeptide, in particular surfactin, at a concentration of 100 mg/l to 2000 mg/l, preferably 500 mg/l to 700 mg/l, particularly preferably 600 mg/l. The use of Dulbecco's phosphate buffered saline (DPBS) without calcium and magnesium as the carrier solution for the detergent surfactin is particularly advantageous. Other biological buffer solutions, such as Tris(hydroxymethyl)aminomethane (TRIS)- or 2-(4-(2-hydroxyethyl)-1-piperazinyl)-ethanesulfonic acid (HEPES)-buffered solutions are also advantageous.

The present invention further relates to the use of a solution containing at least one lipopeptide having amphiphilic properties, comprising a hydrophilic basic structure and a hydrophobic side chain, as the detergent for the decellularization of biological tissue, in particular biological tissue for heart valve prostheses. According to the invention, a solution containing at least one lipopeptide is not used for conditioning, but rather is used for the decellularization and purification of biological tissue.

Surprisingly, it has been shown that solutions containing lipopeptides decellularize biological tissue in a thorough yet gentle manner.

The use of a solution containing, at least, surfactin, daptomycin, caspofungin, arthrofactin, an echinocandin, an iturin, a syringomycin, a syringopeptide, and/or a polymyxin as the detergent for the decellularization of biological tissue is particularly advantageous.

It is advantageous for surfactin, daptomycin, caspofungin, arthrofactin and/or an echinocandin, iturin, syringomycin, syringopeptide, polymyxin to be dissolved in a buffer solution, in particular a phosphate buffer solution. TRIS- or HEPES-buffered solutions are also advantageous.

The present invention provides, in particular, a method for preparing biological tissue, which ensures thorough and reliable decellularization, which is simultaneously implemented in a manner that is gentle on tissue such that the mechanical properties of the tissue, after decellularization and cross-linking, are markedly improved over the prior art.

The method according to the invention for the preparation of biological tissue, in particular for the preparation of biological tissue for use in a heart valve prosthesis, minimizes the risk of calcification of the tissue (and, therefore, the prosthesis) in clinical use. The properties of the tissue are positively influenced in a decisive manner by the detergent for decellularization that is used according to the invention. A tissue that has been prepared using the method according to the invention exhibits markedly improved mechanical strainability.

DETAILED DESCRIPTION OF PREFERRED EMBODIMENTS

The invention is explained in greater detail in the following by reference to exemplary embodiments in the figures and is compared with a method according to the prior art.

In one exemplary embodiment of the invention, a biological tissue is obtained from porcine pericardial tissue by mechanical removal of adhering foreign tissue and subsequent rinsing in isotonic saline solution (Fresenius-Kabi) for 20 hours. This tissue is subjected to decellularization with a detergent comprising a DPBS solution without calcium/magnesium (Lonza; DPBS w/o Ca++/Mg++; Art. No. 17-512)

and surfactin (Sigma-Aldrich, surfactin from *Bacillus subtilis*, Art. No. F3523) in a concentration of 600 mg/l.

The aforementioned exemplary embodiment according to the present invention is compared with two detergents according to the prior art.

In the first example according to the prior art, the biological tissue is subjected to decellularization with a detergent containing sodium dodecyl sulfate (SDS; Sigma-Aldrich, Art. No. L3771) in a concentration of 5 g/l. The solvent used in this case as well is DPBS solution without calcium/magnesium (Lonza; DPBS w/o Ca++/Mg++; Art. No. 17-512).

In a second example according to the prior art, the biological tissue is subjected to decellularization with a detergent containing deoxycholic acid (DCA; Sigma-Aldrich, Art. No. D6750) in a concentration of 10 g/l. Isotonic saline solution (Fresenius-Kabi) is used as the solvent in this case.

Figure 1:
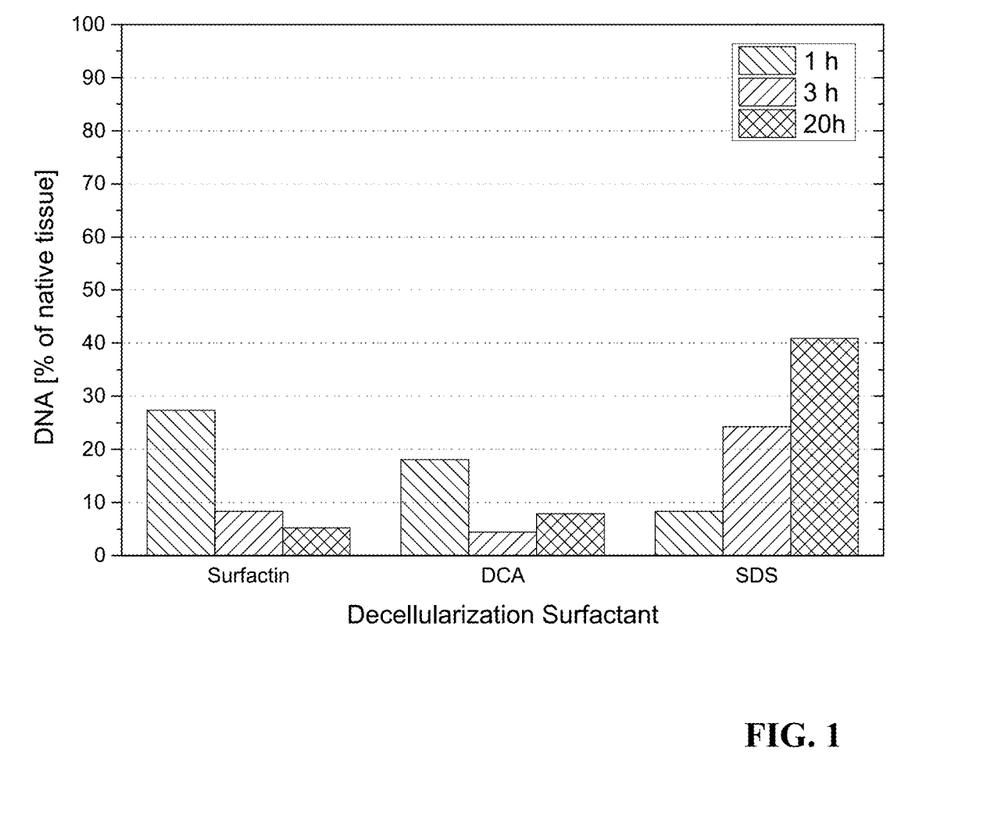
FIG. 1 is a chart depicting a comparison of the DNA content of decellularized tissue treated with surfactin, DCA or SDS.

FIG. 1 shows the comparison of the DNA content after decellularization between the exemplary embodiment according to the invention and the two examples according to the prior art. In FIG. 1, the DNA content of the pericardial tissue after decellularization is plotted on the ordinate in % of the original DNA content before decellularization. In each case, the DNA content was plotted after the biological tissue had been in the respective washing solution for 1 hour, 3 hours, and 20 hours. The DNA content is a direct measure of the removal of cellular components from the biological tissue.

With the aid of the detergent for decellularization containing DCA, the DNA content is reduced to approximately 4% after three hours. As is evident in FIG. 1, the DNA content can be reduced to a similar value after 20 hours in the surfactin-containing detergent of the exemplary embodiment of the invention. The extent of decellularization of pericardial tissue achieved with surfactin within 20 hours corresponds to that of deoxycholic acid. The values of the DNA content for the detergent containing SDS are comparable in this case only to a limited extent, since SDS induces a very pronounced structual change of proteins and massively impairs the DNA detection method, with clearly visible decellularization.

Figure 2:
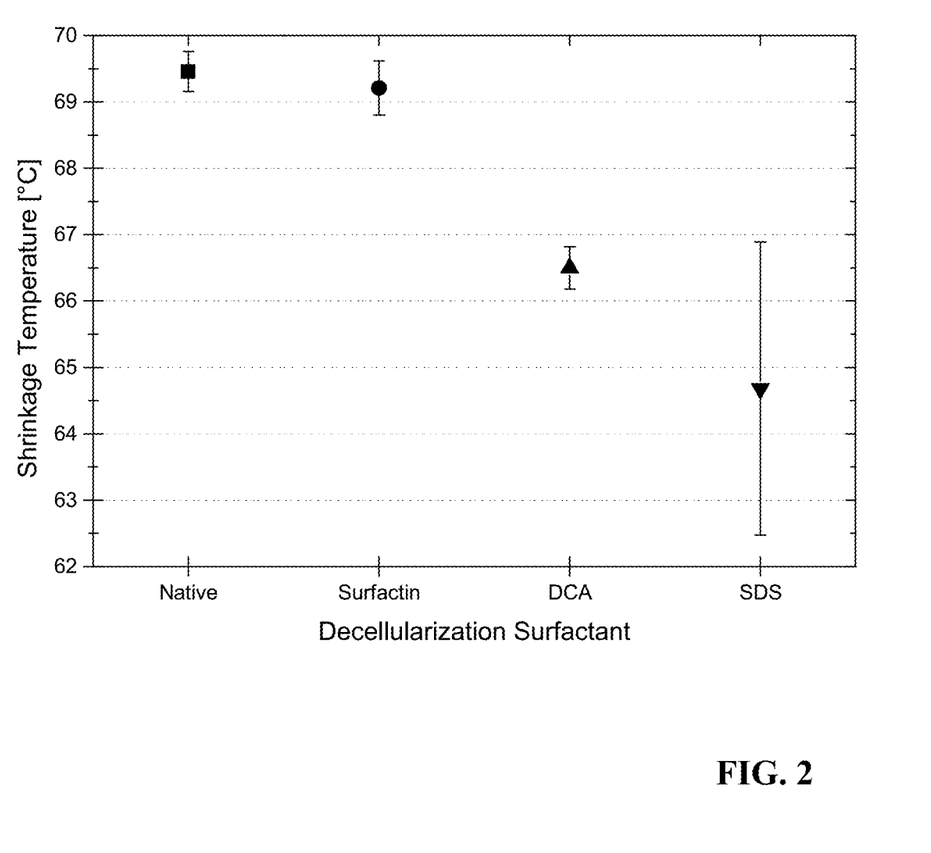
FIG. 2 is a chart depicting the shrinkage temperature of the decellularized tissue after treatment with surfactin, DCA or SDS compared to the shrinkage temperature of native tissue.
Figure 3A:
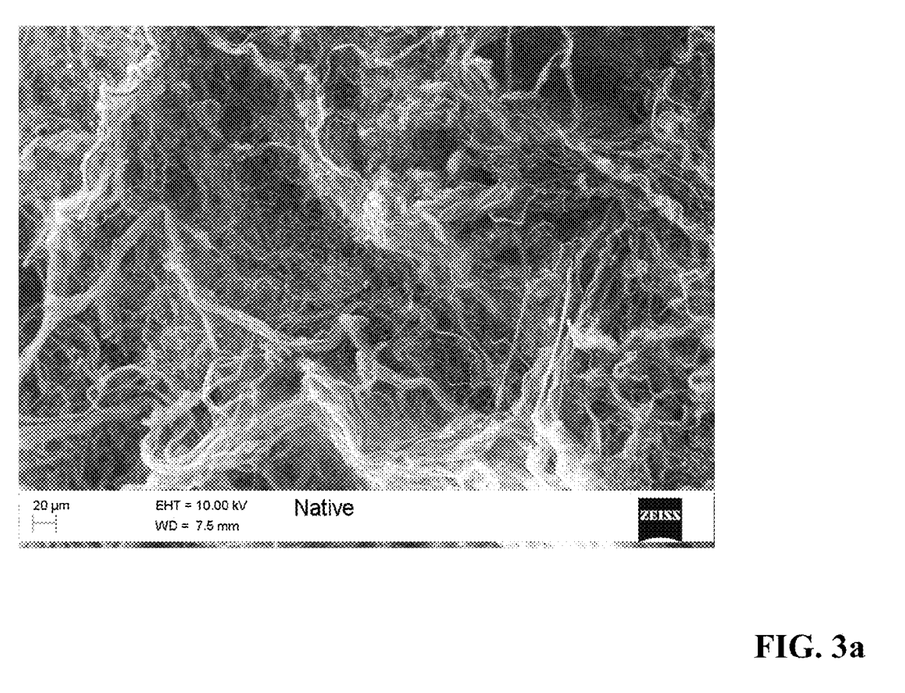
FIGS. 3a-3d are electron-microscopic images of native tissue (FIG. 3a), and decellularized tissue treated with surfactin (FIG. 3b), DCA (FIG. 3c) and SDS (FIG. 3d).
Figure 3B:
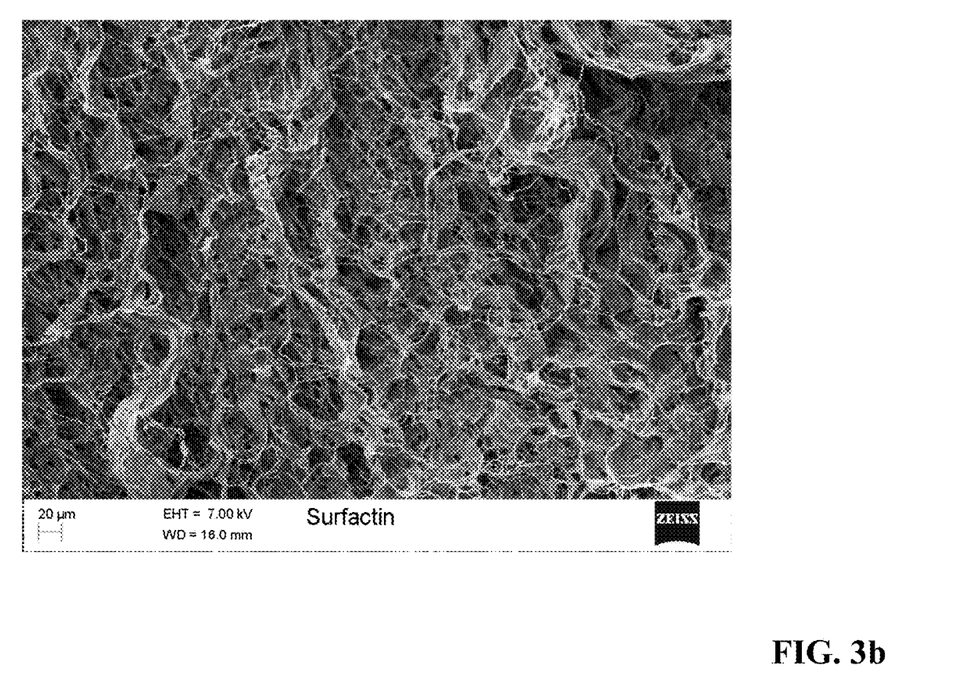
Figure 3C:
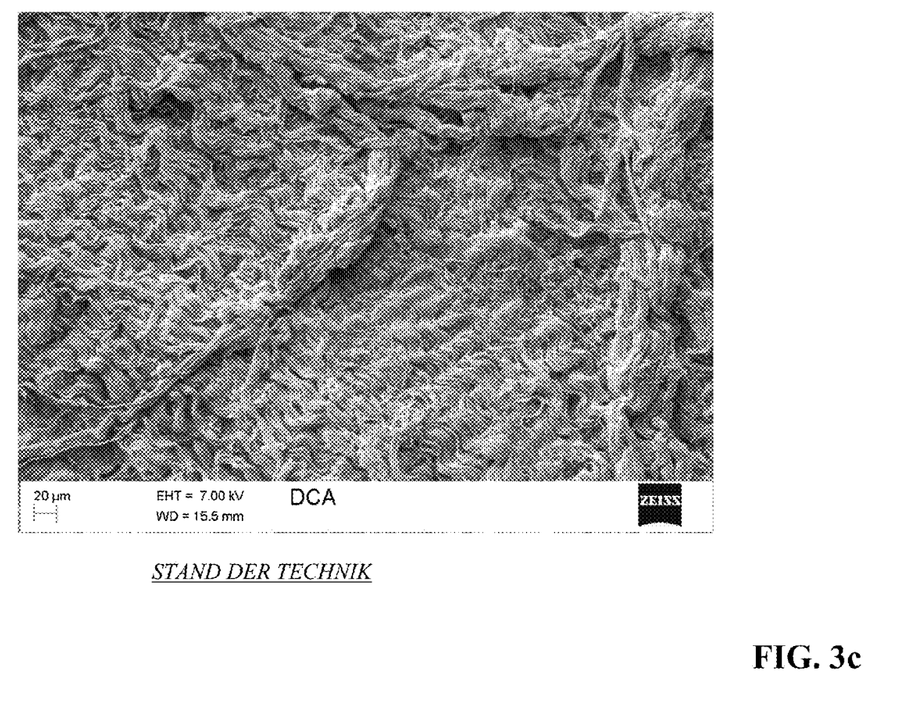
Figure 3D:
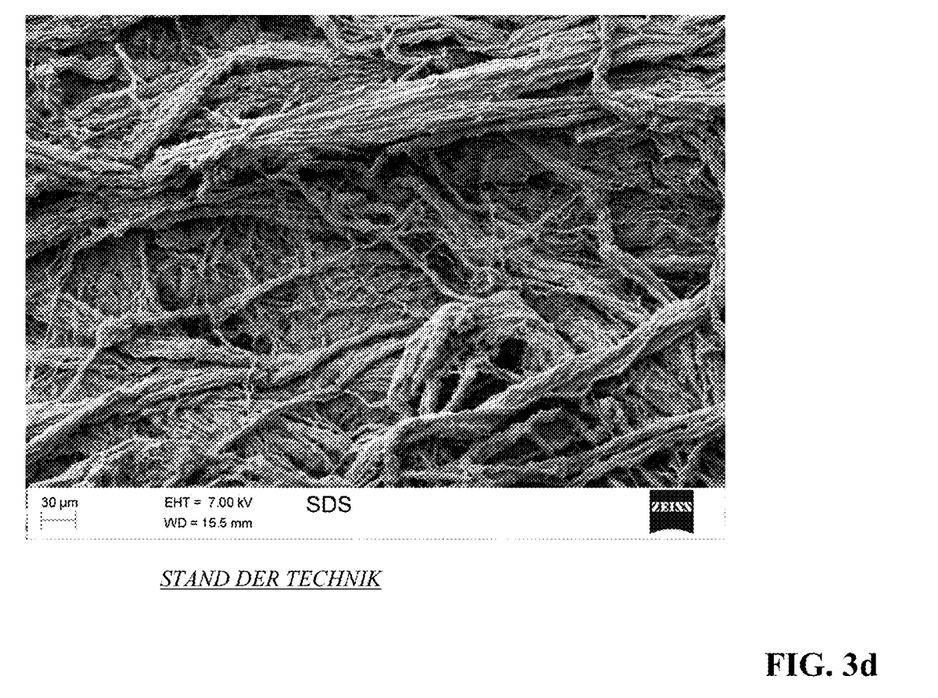

The serious advantages of the method according to the invention compared to decellularization processes according to the prior art are shown in FIGS. 2 to 3d.

FIG. 2 shows, on the ordinate (enlarged scale, zero point not shown), the shrinkage temperature of the decellularized tissue after treatment with the three aforementioned detergents as compared to the shrinkage temperature of the native tissue.

Due to the dominant portion of collagen in the extracellular matrix of pericardial tissue, the shrinkage temperature is the temperature at which the protein thermally denatures collagen, i.e. irreversibly changes the spatial structure thereof. As a result of the structural change of the collagen molecules, the tissue undergoes massive, irreversible structural changes, which become less pronounced, as is clearly visible, when the shrinkage temperature is reached.

The shrinkage temperature was determined in experimentation by means of differential scanning calorimetry (DSC). In this method, the temperature of the sample to be measured is increased linearly over time and the flow of heat into or out of the sample is measured relative to a reference sample. If thermodynamic processes occur in the sample, e.g. the irreversible structural change of the collagen, a distinct peak forms at the shrinkage temperature in the thermogram that is measured. The level of the shrinkage temperature is a direct indicator of the stability of the spatial structure of the collagen molecules. The least possible change compared to the state in native tissue is therefore a direct indication, at the molecular level, of the markedly more gentle decellularization by surfactin.

As is clearly evident in FIG. 2, the shrinkage temperature of the pericardial tissue after decellularization according to the exemplary embodiment of the invention is nearly identical to the shrinkage temperature of the untreated native pericardial tissue. The decellularization according to the two exemplary embodiments of the prior art with DCA and SDS, however, result in a shrinkage temperature that is markedly reduced, by 3° C. and 5° C., respectively, and, therefore, to a markedly impaired tissue structure. The mechanical properties of the native biological tissue and the tissue after decellularization according to the invention are therefore very similar. With the aid of the method according to the invention, the decellularization therefore takes place in a very gentle method, as demonstrated.

The different impairment of the tissue structure is also shown in the electron-microscopic images of the native tissue and the tissue after decellularization with the aforementioned detergents, wherein these images are shown in FIGS. 3a-d.

The images exhibit great similarity in the comparison of the native tissue in FIG. 3a with the decellularized tissue according to the aforementioned exemplary embodiment of the invention in FIG. 3b. Both tissues show a plurality of collagen fibers and strands that are separated from one another.

By comparison, the tissue shown in FIGS. 3c and 3d is markedly changed after decellularization with the stated detergents according to the prior art. Smaller collagen fibers, in particular, tend to attach themselves to one another in this case. As a result, the tissue structure is markedly changed and, in the electron-microscopic images, appears to be much more compact.

Figure 4:
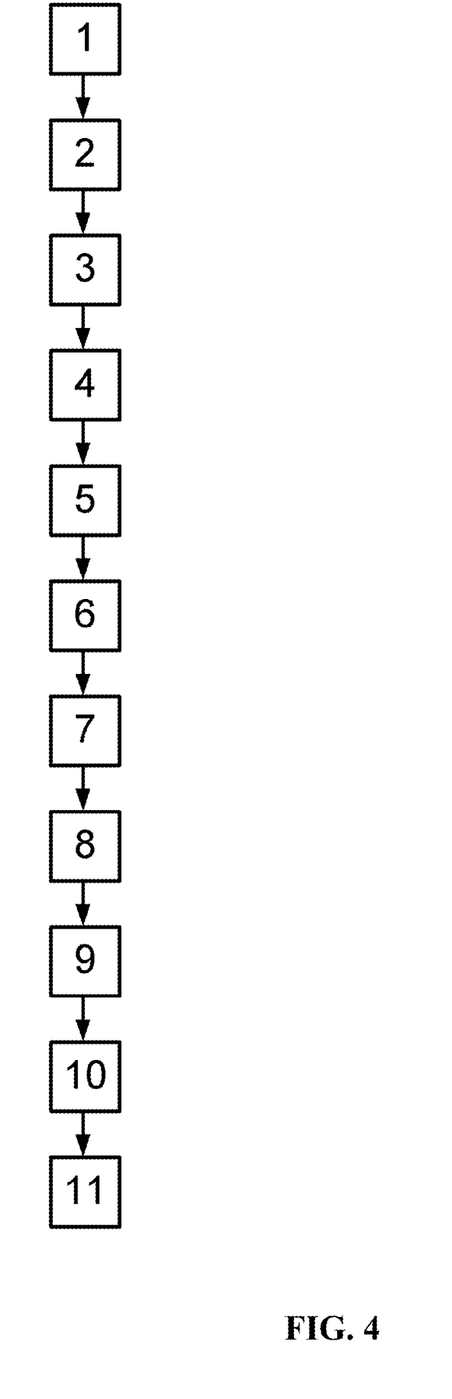
FIG. 4 is a flow chart depicting the order of 11 steps for preparing biological tissue for implantation according to the present invention.

FIG. 4 shows an embodiment of a complete method for preparing biological tissue for implantation applications according to the present invention.

In step 1, a pericardium is removed from a pig in a slaughterhouse and is stored in a sterile isotonic sodium chloride solution (9 g/l; Fresenius-Kabi) at a temperature of 4° C. for 2 hours. The solution contains sodium chloride as well as penicillin and/or streptomycin to kill bacterial germs.

In step 2, the tissue is prepared, moist, in a sodium chloride solution (9 g/l; Fresenius-Kabi). That is, the layers of the pericardium are separated from one another, adhering fatty and connective tissue is carefully removed, and the tissue is cut to the size and shape for the desired application.

After rinsing with a sodium chloride solution (9 g/l; Fresenius-Kabi) with slight movement of the tissue in step 3, the tissue is decellularized in step 4.

The decellularization in step 4 takes place with a detergent comprising a buffer solution containing surfactin. In this exemplary embodiment of the invention, surfactin (Sigma-Aldrich, surfactin from *Bacillus subtilis*, Art. No. F3523) having a concentration of 600 mg/l is dissolved in a DPBS phosphate buffer solution (Lonza; DPBS w/o Ca++/Mg++; Art. No. 17-512). The tissue remains in this washing solution for 20 hours at 37° C. The tissue is then cleaned nearly entirely of cellular components located therein without substantially changing the structure of the collagen fibers.

In the subsequent steps 5, 6 and 7, the decellularized tissue is thoroughly rinsed in sterile solutions. In step 5, the tissue is rinsed, with slight movement, in 100 ml sodium chloride solution (9 g/l; Fresenius-Kabi) at room temperature. In this exemplary embodiment of the invention, step 5 is carried out for 10 minutes and is repeated 8 times. In step 6, the tissue is then rinsed with 100 ml of a 70% ethanol solution for 10 minutes at 37° C. In step 7, the tissue is rinsed once more in 100 ml sodium chloride solution (9 g/l; Fresenius-Kabi) with slight movement.

In step 8, the collagen fibers are cross-linked with a cross-linking agent. In this exemplary embodiment of the invention, the tissue is placed in a solution containing glutaraldehyde (Sigma-Aldrich, Art. No. F5882) at pH 7.4 for 48 hours at a temperatuare of 4° C. The solution containing glutaraldehyde comprises glutaraldehyde in a concentration of 6 g/l in DPBS without calcium and magnesium (Lonza; DPBS w/o Ca++/Mg++; Art. No. 17-512).

Step 9 repeats step 8 at room temperature. Step 9 is carried out for 14 days, and the solution is replaced every 48 hours.

After a rinsing process in step 10, the tissue can be stored in glutaraldehyde or can be processed further in step 11. In step 10, the tissue in this exemplary embodiment of the invention is rinsed with 100 ml sodium chloride solution (9 g/l; Fresenius-Kabi), with slight movement, for 20 minutes at room temperature.

The exemplary embodiment described here is intended to clarify the invention. The number and/or design of the rinsing steps (in particular the concentration and composition of the solution for rinsing, or of the buffer solution) can be varied by a person skilled in the art as he sees fit.

What is claimed is:

1. A method for preparing tissue for medical applications, comprising:
   decellularizing the tissue by means of a detergent, characterized in that the decellularizing detergent contains at least one amphiphilic lipopeptide comprising a hydrophilic base structure and a hydrophobic side chain; and subsequently
   cross-linking the collagen fibers of the tissue by means of a suitable cross-linking agent.

2. The method according to claim 1, characterized in that the decellularizing detergent contains a cyclic lipopeptide.

3. The method according to claim 2, characterized in that the cyclic lipopeptide is surfactin.

4. The method according to claim 1, characterized in that the detergent contains surfactin, daptomycin, caspolungin, arthrofactin, an echinocandin, an iturin, a syringomycin, a syringopeptide, and/or a polymyxin.

5. The method according to claim 1, characterized in that the cross-linking agent contains glutaraldehyde, a carbodilmide, formaldehyde, a glutaraldehyde acetal, an acyl azide, a cyanimide, genipin, a tannin, pentagalloyl glucose, a phytate, a proanthocyanidin, reuterin and/or an epoxide compound.

6. The method according to claim 1, characterized in that the tissue is rinsed before and/or after decellularization at least once with a suitable solvent.

7. The method according to claim 1, characterized in that the detergent comprises a buffer solution and said at least one amphiphilic lipopeptide.

8. The method according to claim 7, characterized in that the lipopeptide is surfactin at a concentration in said detergent of 100 mg/L to 2000 mg/L.

9. The method according to claim 8, wherein the surfactin is at a concentration in said detergent of 500 mg/L to 700 mg/L.

10. The method according to claim 1, wherein the tissue is for an artificial heart valve.

\* \* \* \* \*